(12) United States Patent
Wang et al.

(10) Patent No.: US 7,724,869 B2
(45) Date of Patent: May 25, 2010

(54) DETECTOR ARRAY AND DEVICE USING THE SAME

(75) Inventors: Xuewu Wang, Beijing (CN); Zhiqiang Chen, Beijing (CN); Yuanjing Li, Beijing (CN); Huaqiang Zhong, Beijing (CN); Qingjun Zhang, Beijing (CN); Shuqing Zhao, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 73 days.

(21) Appl. No.: 11/789,095

(22) Filed: Apr. 23, 2007

(65) Prior Publication Data

US 2007/0286337 A1 Dec. 13, 2007

(30) Foreign Application Priority Data

May 19, 2006 (CN) .................... 2006 1 0011943

(51) Int. Cl.
*G01N 23/087* (2006.01)

(52) U.S. Cl. .................... 378/57; 378/53; 378/98.8; 378/98.9; 378/98.11

(58) Field of Classification Search .................... 378/5, 378/16, 53, 57, 98.9, 19, 98.8, 98.11
See application file for complete search history.

(56) References Cited

U.S. PATENT DOCUMENTS

| | | | |
|---|---|---|---|
| 4,242,583 A * | 12/1980 | Annis et al. | 378/146 |
| 5,012,498 A | 4/1991 | Cuzin et al. | 378/22 |
| 5,044,002 A | 8/1991 | Stein | 378/54 |
| 5,524,133 A | 6/1996 | Neale et al. | 378/53 |
| 5,583,904 A * | 12/1996 | Adams | 378/22 |
| 5,661,774 A * | 8/1997 | Gordon et al. | 378/101 |
| 5,841,832 A * | 11/1998 | Mazess et al. | 378/56 |
| 6,069,936 A | 5/2000 | Bjorkholm | 378/98.9 |

(Continued)

FOREIGN PATENT DOCUMENTS

DE 3629180 A1 8/1986

(Continued)

OTHER PUBLICATIONS

Germany Office Action from related DE Application No. 102007020545.9; date Sep. 5, 2007; 4 pages.

(Continued)

*Primary Examiner*—Allen C. Ho
(74) *Attorney, Agent, or Firm*—Westman, Champlin & Kelly, P.A.

(57) ABSTRACT

Disclosed is a detector array comprising a first linear array for detecting a first ray and a second ray which penetrate through a first plurality of parts of the inspected object to acquire first values and second values for the first plurality of parts, wherein the second ray is alternately emitted with the first ray; and a second linear array arranged parallel to the first linear array for detecting the first ray and the second ray which penetrate through a second plurality of parts of the inspected object to acquire third values and fourth values for the second plurality of parts, wherein the first plurality of parts is partly identical to the second plurality of parts. With the detector array, the efficiency and material discrimination accuracy can be improved in the scanning inspection of the inspected object by use of alternate dual-energy rays.

13 Claims, 4 Drawing Sheets

U.S. PATENT DOCUMENTS

| | | | |
|---|---|---|---|
| 6,188,747 B1 * | 2/2001 | Geus et al. | 378/124 |
| 6,198,795 B1 * | 3/2001 | Naumann et al. | 378/57 |
| 6,236,709 B1 * | 5/2001 | Perry et al. | 378/57 |
| 6,370,223 B1 * | 4/2002 | Gleason et al. | 378/58 |
| 6,553,092 B1 * | 4/2003 | Mattson et al. | 378/19 |
| 6,580,778 B2 * | 6/2003 | Meder | 378/57 |
| 6,600,805 B2 * | 7/2003 | Hansen | 378/53 |
| 7,020,241 B2 * | 3/2006 | Beneke et al. | 378/57 |
| 7,319,737 B2 * | 1/2008 | Singh | 378/57 |
| 2004/0264628 A1 | 12/2004 | Besson | 378/5 |
| 2005/0067570 A1 | 3/2005 | Retterath et al. | 250/359.1 |

FOREIGN PATENT DOCUMENTS

| | | |
|---|---|---|
| EP | 1355321 A2 | 10/2003 |
| GB | 0709609.2 | 8/2007 |
| JP | 3102698 | 10/2000 |
| JP | 2001-99790 | 4/2001 |
| JP | 2007-309929 | 11/2007 |
| WO | WO 99/08132 | 2/1999 |
| WO | WO 00/43760 | 7/2000 |
| WO | WO 2004/030162 A2 | 4/2004 |
| WO | WO 2004/054329 | 6/2004 |
| WO | WO 2004/079659 | 9/2004 |

OTHER PUBLICATIONS

Chinese application No. 2000610011943X; date stamped 2009.06.26.00; 6 pages.

United Kingdom Office Action from related UK Application No. GB0709609.2; dated Aug. 17, 2007, 6 pages.

Japanese Office Action from related Japanese application No. 2007-124981; 4 pages.

* cited by examiner

DETECTOR ARRAY AND DEVICE USING THE SAME

FIELD OF THE INVENTION

The present invention relates to a detector for radiograph imaging of an object, and more particularly, to a detector array and a device using the same, which can eliminate error and inaccuracy of material discrimination at the edge occurring during the process of the object inspection using alternately generated rays, and can improve the efficiency of scanning inspection by multiples.

BACKGROUND OF THE INVENTION

The present application claims priority of Chinese patent application Serial No. 200610011943.X, filed May 19, 2006, the content of which is hereby incorporated by reference in its entirety.

As the requirement for a security inspection system such as at Customs is constantly increased, the relevant technology has been widely applied as in U.S. Pat. No. 5,044,002, in which X-rays having two different energy levels are utilized to perform non-destructive inspection on an object while the material of the object is identified. Recently, the dual-energy method is resumed to implement material identification within high-energy range (>1 MeV) in the non-destructive inspection of large-sized objects, as disclosed in U.S. Pat. No. 5,524,133.

The physical principle of the dual-energy method for discriminating material is that when two X-ray beams having different energy levels interact with the same object, since the photon energy levels of the two beams are different from each other, there exists a difference between their interactions with the object. Such difference as a whole can simply be represented by the difference in attenuation index. Based on such principle various methods of alternately generating X-rays having two energy levels have been proposed, such as in U.S. Pat. No. 6,069,936 and international application WO 00/43760 there is disclosed a single radiation source which modulates a high energy spectrum by means of material absorption. In addition, international application WO 2004/030162 A2 discloses a method of alternately generating X-rays having high and low energy spectra by an accelerator. However, when the alternately generated X-rays having high and low energy spectra are utilized to scan an object, a severe defection occurs as follows. Since the X-rays having two energy levels are alternately generated at certain frequency, there is certain time interval between the generation of each ray. The inspected object always move at certain speed, and thus it will move by some distance during the time interval between the generation of X-rays having high and low energy levels. Therefore, when used to scan the inspected object (e.g., luggage, container, etc.), the interactions between the two kinds of X-rays and the object are not completely identical. This will have a negative impact on the discrimination accuracy, especially at the edge of the inspected object where the rays having two energy levels may interact with different objects, thereby incurring a false discrimination result. Meanwhile, in order to suppress the error due to rays having high and low energy levels interacting with different positions, the conventional method is to slow down the movement of the inspected object. This method severely limits the efficiency of object inspection and can't solve the false discrimination occurring at the edge of the object.

SUMMARY OF THE INVENTION

In view of the above problem with the prior art, the present invention is accomplished. It is an object of the present invention to provide a detector array and a material discrimination system using this detector array, which can suppress discrimination errors occurring at the edge of the inspected object during the process of object inspection utilizing rays alternately generated.

At the first aspect of the present invention, there is provided a detector array comprising: a first linear array for detecting a first ray and a second ray which penetrate through a first plurality of parts of the inspected object to acquire first values and second values for the first plurality of parts, wherein the second ray is alternately emitted with the first ray; and a second linear array arranged parallel to the first linear array for detecting the first ray and the second ray which penetrate through a second plurality of parts of the inspected object to acquire third values and fourth values for the second plurality of parts, wherein the first plurality of parts is partly identical to the second plurality of parts.

According to an embodiment of the present invention, the first linear array is arranged closely to the second linear array.

According to an embodiment of the present invention, the distance between the first linear array and the second linear array is adjustable.

According to an embodiment of the present invention, the distance depends on the moving speed of the inspected object and the time interval between the alternate generation of the first ray and the second ray.

According to an embodiment of the present invention, each detector element of the first linear array and the second linear array comprises a scintillator or a gas detector.

According to an embodiment of the present invention, the first linear array and the second linear array are both connected to the same processing apparatus.

According to an embodiment of the present invention, each of the first linear array and the second linear array is connected to respective processing apparatuses.

According to an embodiment of the present invention, the first ray and the second ray are generated by the same radiation source.

According to an embodiment of the present invention, the scintillator is $CdWO_4$ or CsI.

In addition, the present invention further provides a device comprising the detector array described above.

The present invention further provides a radiograph imaging method utilizing the detector array described above.

The present invention further provides a material identification method utilizing the detector array described above.

At another aspect of the present invention, there is provided a method of detecting rays with a detector array comprising a first linear array and a second linear array arranged parallel to each other, the method comprises the steps of: generating alternately a first ray and a second ray to penetrate through an inspected object moving at a fixed speed; detecting the first ray and the second ray which penetrate through a first plurality of parts of the inspected object with the first linear array, to acquire first values and second values for the first plurality of parts, wherein the second ray is alternately emitted with the first ray; and detecting the first ray and the second ray which penetrate through a second plurality of parts of the inspected object with the second linear array, to acquire third values and fourth values for the second plurality of parts, wherein the first plurality of parts is partly identical to the second plurality of parts.

According to an embodiment of the present invention, the method further comprises adjusting the distance between the first linear array and the second linear array based on the moving speed of the inspected object and the time interval between the alternate generation of the first ray and the second ray.

At another aspect of the present invention, there is provided a detector array comprising: a first linear array for detecting a first ray, a second ray and a third ray which penetrate through a first plurality of parts of the inspected object to acquire first values, second values and third values for the first plurality of parts, wherein the first ray, the second ray and the third ray are alternately emitted; a second linear array arranged parallel to the first linear array for detecting the first ray, the second ray and the third ray which penetrate through the second plurality of parts of inspected object to acquire fourth values, fifth values and sixth values for the second plurality of parts, wherein the first plurality of parts are partly identical to the second plurality of parts; and a third linear array arranged parallel to the first linear array and the second linear array for detecting the first ray, the second ray and the third ray which penetrate through a third plurality of parts of the inspected object to acquire seventh values, eighth values and ninth values for the third plurality of parts, wherein the second plurality of parts are partly identical to the third plurality of parts.

It is possible to make the ray beams having high and low energy levels interact with the object at the same position and realize accurate detection by utilizing the above detector array to detect the penetrating rays as well as by using dislocation matching. Meanwhile, since the distance between the first linear array and the second linear array is determined based on the moving speed of the inspected object and the time interval between the generation of rays having high and low energy levels by the radiation source, the rays interacting with the inspected object at the same part are ensured to be detected, thereby improving the accuracy of the dual-energy method in discriminating material and suppressing the false discrimination result at the edge of the inspected object. Because the distance between the first linear array and the second linear array is adjustable, the moving speed of the inspected object is variable. Therefore, the requirement for the moving speed of the inspected object is decreased. Moreover, since the first linear array and the second linear array simultaneously collect signals, the detective area is equivalently increased. On the other hand, the small section of the individual scintillator ensures to detect objects with high detection precision and obtain detailed detective images.

DETAILED DESCRIPTION OF THE PREFERRED EMBODIMENTS

Hereafter, an embodiment of the present invention is described in detail with reference to the drawings.

Figure 1:
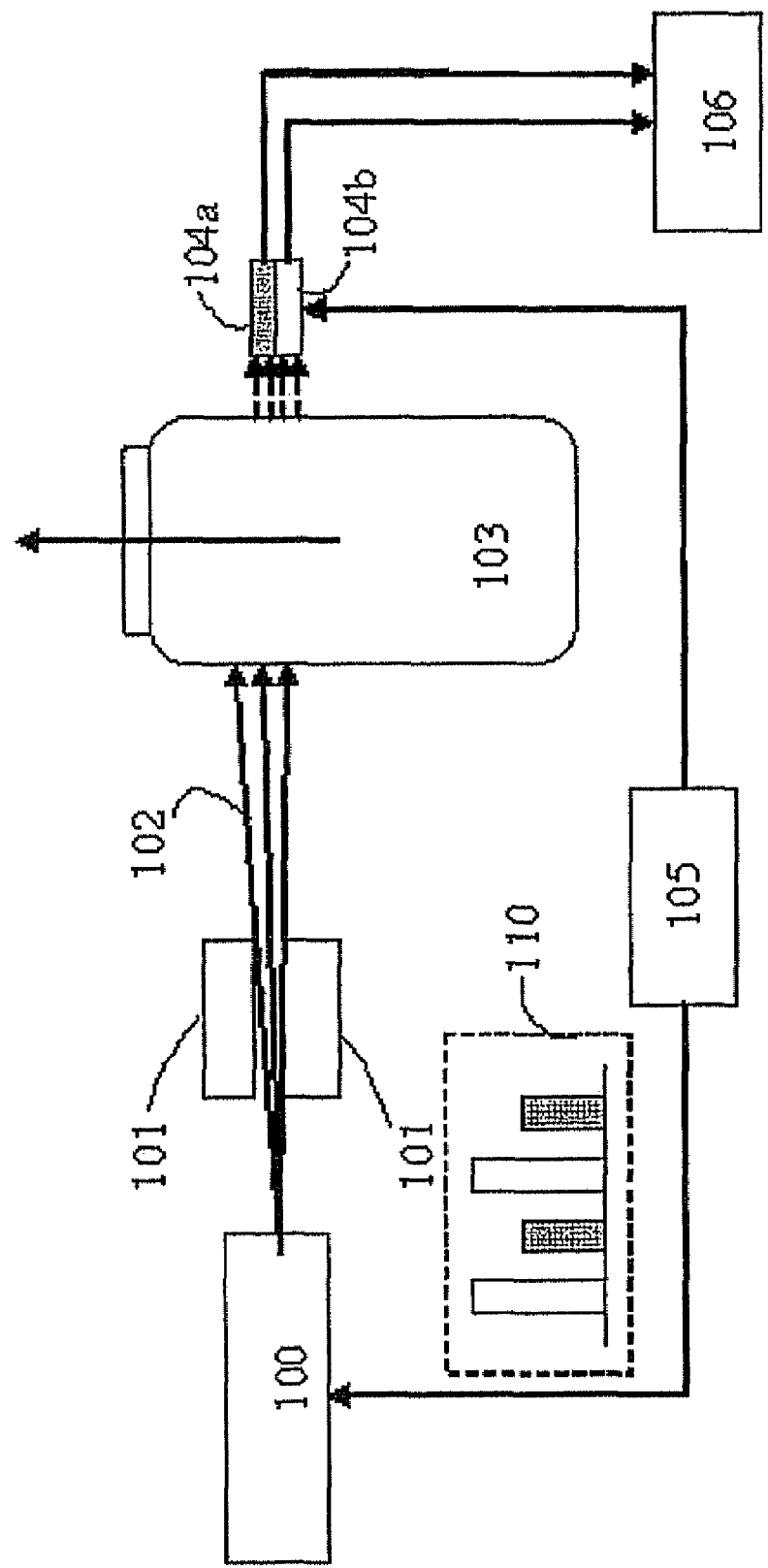
FIG. 1 is the schematic view of the material identification system using a detector array according to an embodiment of the present invention.

FIG. 1 is the schematic view of the material discrimination system using a detector array according to an embodiment of the present invention.

As shown in FIG. 1, the detector array including the first linear array 104a and the second linear array 104b is used to collect the dual-energy rays generated alternately by a radiation source. The radiation source 100 can alternately generate radiations such as X-rays. The synchronization control part 105 provides a synchronization signal 110 for the radiation source 100 and the first and second linear arrays 104a and 104b to make the radiation source 100 alternately generate high- and low-energy-level rays at the timing of the synchronization signal 110.

A fan-shaped planar radiation is obtained after the rays 102 generated by the radiation source 100 pass through the collimator 101. As shown in FIG. 1, the inspected object 103 moves at a fixed speed in a fixed direction perpendicular to the radiation plane. The penetrating radiation after the interaction between the planar radiation and the inspected object 103 is detected by the first and second linear arrays 104a and 104b. Here, the first and second linear arrays 104a and 104b are arranged parallel to each other, and based on the synchronization signal from the synchronization control part 105, adjust the parameters of the collecting circuits to perform simultaneous collecting. However, this isn't necessary.

Then, the processing module of the dual-column detector array matches the newly collected signals of the two ray beams and outputs the detection values obtained after the high- and low-energy rays interact with the inspected object 103. The detection values are sent to the image processing and material discrimination part 106 via the network. The image processing and material discrimination part 106 finally identify the material property of the inspected object such as inorganic matter, organic matter, heavy metal, etc. by use of the dual-energy algorithm and the relevant image processing algorithm.

Figure 2:
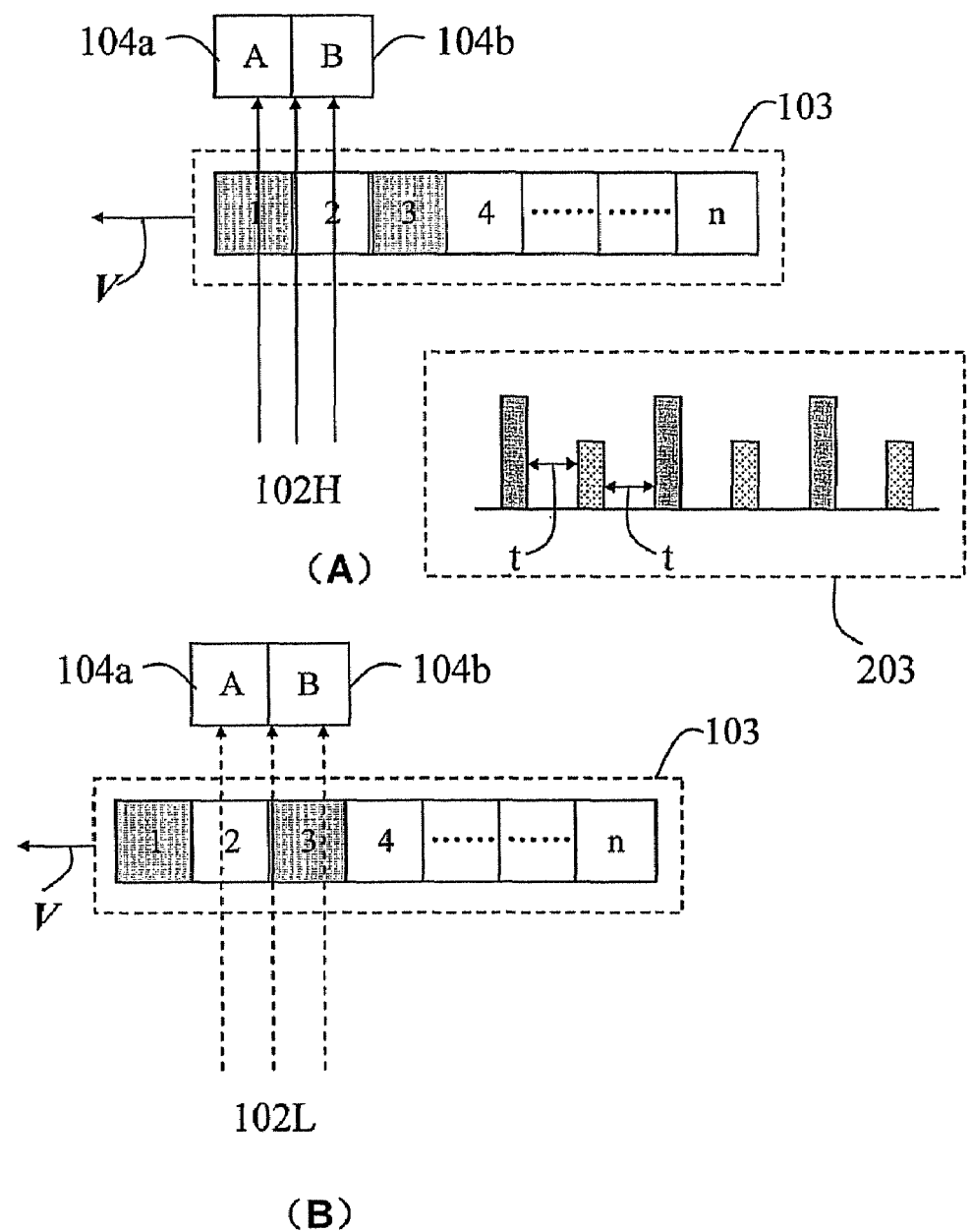
FIG. 2 is the schematic view showing the operating principle of the detector array when a radiation source alternately generates rays having different energy levels according to an embodiment of the present invention.

FIG. 2 is the schematic view showing the operating principle of the detector array when the radiation source 100 alternately generates rays having different energy levels according to the embodiment of the present invention.

As shown in FIG. 2, on the basis of the timing 203, the radiation source 100 alternately generates rays 102H and 102L having high and low energy levels, which are alternately emitted at a fixed frequency with the time intervals t between the emission of two ray beams are equal. The object 103 moves at a fixed speed along certain direction. It is assumed that the radiation source 100 emits a high-energy ray 102H, which is collimated and then interacts with the parts 1 and 2 of the inspected object 103. The penetrating ray is collected and buffered by the first and second linear arrays 104a and 104b, respectively, and the detection values are referred as 102H-1A and 102H-2B.

Then, the radiation source 100 emits a low-energy ray 102L when the time t has elapsed. At this time, the inspected object 103 has moved forward by a distance of one pixel, i.e., V*t. The low-energy ray 102L penetrate through the parts 2 and 3 of the inspected object 103, and is subsequently collected and buffered by the first and second linear arrays 104a and 104b, respectively, with the detection values being referred as 102L-2A and 102L-3B. The processing module of the detector array pairs the previously buffered detection value 102H-2B, which is collected after the high-energy ray 102H interacts with the part 2 of the inspected object 103, and the newly buffered detection value 102L-2A, which is collected after the low-energy ray 102L interacts with the part 2 of the inspected object 103, and outputs the pair to the image processing and material identification part 106.

Next, on the basis of the timing 203, the radiation source 100 generate a high-energy ray 102H again, while the inspected object 103 moves further by a distance of one pixel V*t. Therefore, the high-energy ray 102H interacts with the parts 3 and 4 of the inspected object 103. After such interaction, the detection values are collected respectively by the first and second linear arrays 104a and 104b, and referred as 102H-3A and 102H-4B. Subsequently, the processing module of the detector array pairs the previously buffered detection value 102L-3B, which is collected after the low-energy ray 102L interacts with the part 3 of the inspected object 103, and the newly collected detection value 102H-3A, which is collected after the high-energy ray 102H interacts with the part 3 of the inspected object 103, and outputs the pair to the image processing and material discrimination part 106. In this way, as the inspected object 103 moves, the signal detection is performed after the high- and low-energy rays interact with the same part of the inspected object 103.

Since the paralleled first and second linear arrays 104a and 104b are utilized, the first ray, which is an approximate narrow beam of high energy and first generated by the radiation source 100, can be collected by the first and second linear arrays 104a and 104b after the interaction with the parts 1 and 2 of the inspected object 103. The first linear array 104a detects the first ray penetrating through the part 1 of the inspected object 103 and outputs the first detection value for the part 1, and the second linear array 104b detects the first ray penetrating through the part 2 of the inspected object 103 and outputs the first detection value for the part 2. Immediately following is that the radiation source 100 emits the second ray of a low energy level. Since the inspected object 103 has move forward by a distance of one pixel, the second ray will interact with the part 2 and 3 of the inspected object 103. The first and second linear arrays 104a and 104b detect the signals for the parts 2 and 3 penetrated through by the second ray, and output the second detection value for the part 2 and the first detection value for the part 3, respectively. Accordingly, the first and second detection values for the part 2 are the values outputted after the first and second rays penetrate through the part 2 of the inspected object 103, respectively. Thus, the effective atomic number in the part 2 of the inspected object 103 can be determined based on the first and second detection values for this part, thereby determining the material property of the part 2.

Figure 3:
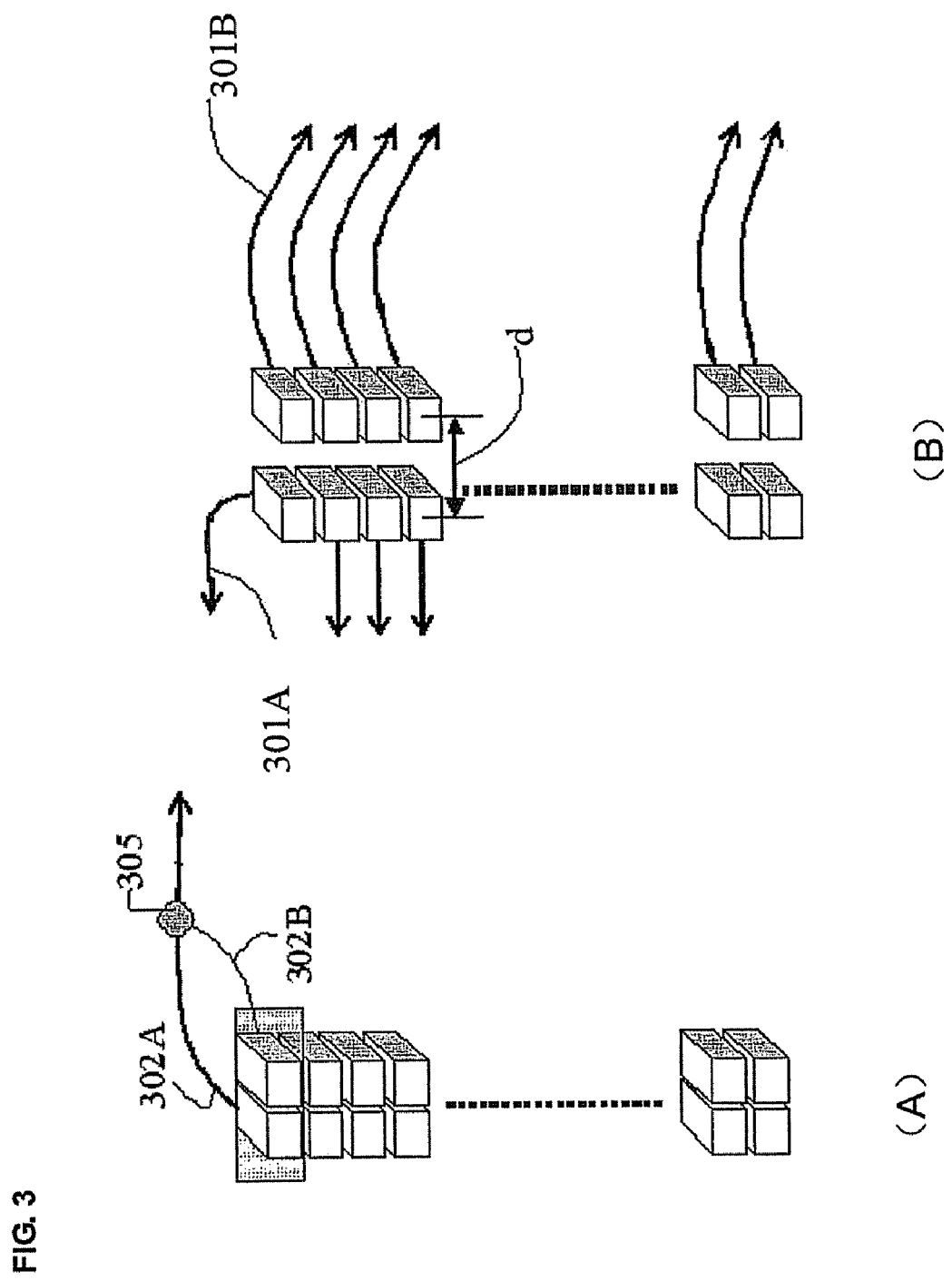
FIG. 3 is the schematic structural view of the detector array according to an embodiment of the present invention.

Here, as shown in FIG. 3(A), the two linear arrays 104a and 104b each comprising a plurality of detector elements and they can be formed of two closely-arranged scintillators, such as $CdWO_4$ and CsI. The first and second linear arrays 104a and 104b can be combined into a whole. The two scintillators of each row are fixed and connected to the processing module 305. After detecting signals, the two crystals simultaneously output the signals 302A and 302B, which are buffered and process in the processing module 305. When the detectors have collected the signals for the high- and low-energy rays upon two adjacent pulses, the processing module 305 matches the signals for the high- and low-energy rays and outputs the high- and low-energy detection values corresponding to the same part of the inspected object to the image processing and material discrimination part 106. As an alternative aspect, the two linear arrays 104a and 104b can independently output the signals 301A and 301B to their own processing modules (not shown), respectively. Every time the detector array collects the signals after the high- or low-energy ray penetrates through the inspected object, the signals are outputted to the processing module 305 so as to pair the detection values for the high- and low-energy rays, thereby obtaining the high- and low-energy detection values for each part of the inspected object 103. As an alternative aspect, each detector element of the two linear arrays can be formed of a gas detector.

Furthermore, the distance d between the first and second linear arrays 104a and 104b is adjustable as shown FIG. 3(B). Here, the distance d is determined by the moving speed V of the inspected object 103 and the time interval t between the generation of high- and low-energy rays by the radiation source, i.e., d=V*t. That is, the distance between the first and second linear arrays is adjusted based on the moving speed of the inspected object and the time interval between the generation of high- and low-energy rays by the radiation source, thereby meeting the need for the adjacent high- and low-energy rays to penetrate through the same part of the inspected object.

It should be noted the two linear arrays could be extended as four or six linear arrays to increase scan speed.

Although the invention has been described in the case of dual energy, the present invention could be applied to multi-energy applications.

Figure 4:
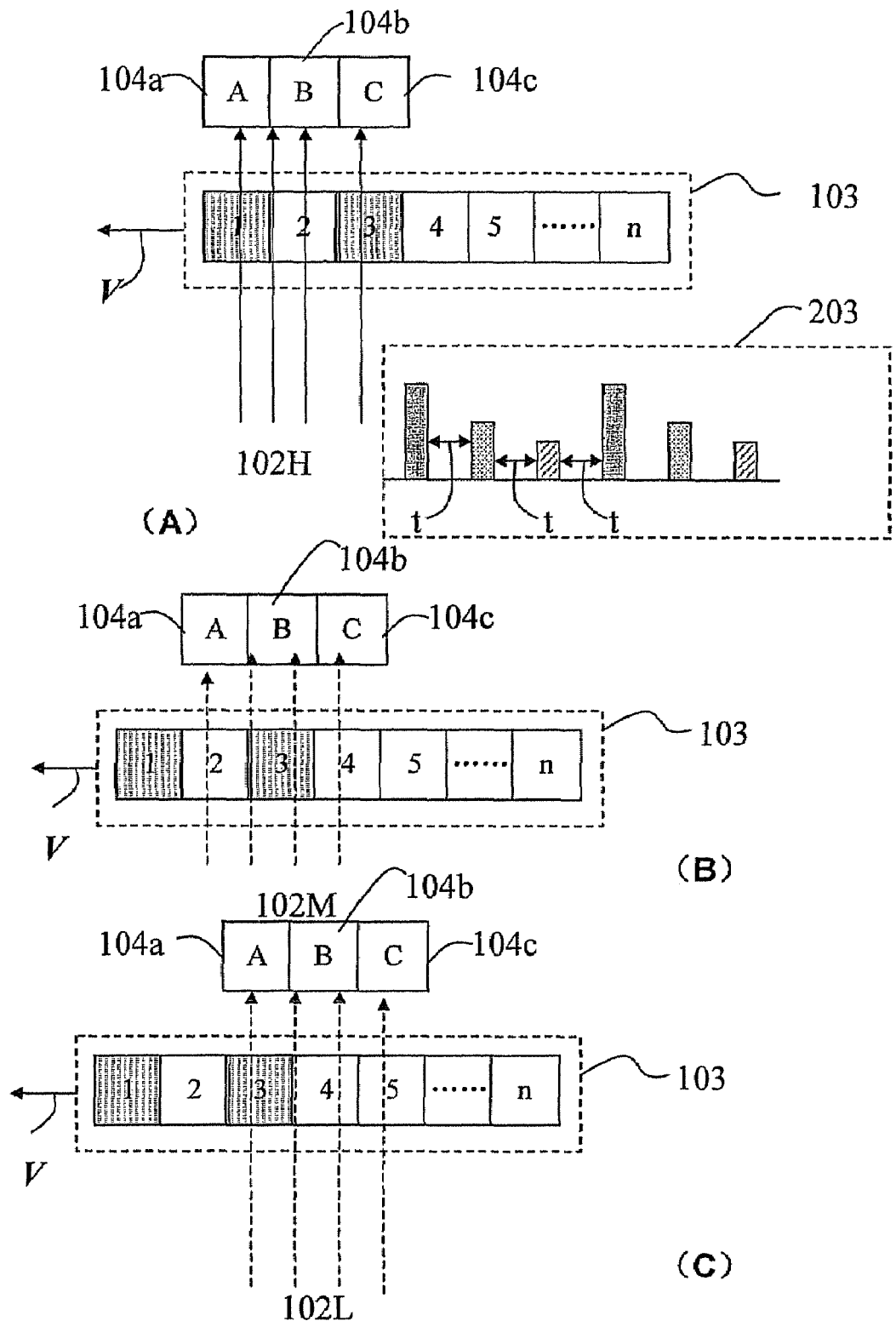
FIG. 4 is the schematic view showing the operating principle of the detector array when a radiation source alternately generates rays having different energy levels according to another embodiment of the present invention.

FIG. 4 is the schematic view showing the operating principle of the detector array when a radiation source alternately generates rays having different energy levels according to another embodiment of the present invention.

As shown in FIG. 4, the present embodiment differs from the previous embodiment in that the detector array comprises three linear arrays 104a, 104b and 104c corresponding to three rays 102H, 102M and 102L.

As shown in FIG. 4, on the basis of the timing 203, the radiation source 100 alternately generates rays 102H, 102M and 102L having high, medium and low energy levels, which are alternately emitted at a fixed frequency with the time intervals t between the emission of two ray beams are equal. The object 103 moves at a fixed speed along certain direction. It is assumed that the radiation source 100 emits a high-energy ray 102H, which is collimated and then interacts with the parts 1, 2 and 3 of the inspected object 103. The penetrating ray is collected and buffered by the first, second, and third linear arrays 104a, 104b and 104c, respectively, and the detection values are referred as 102H-1A, 102H-2B and 102H-3C.

Then, the radiation source 100 emits a medium-energy ray 102M when the time t has elapsed. At this time, the inspected object 103 has moved forward by a distance of one pixel, i.e., V*t. The medium-energy ray 102M penetrate through the part 2, 3 and 4 of the inspected object 103, and is subsequently collected and buffered by the first, second and third linear arrays 104a, 104b and 104c, respectively, with the detection values being referred as 102M-2A, 102M-3B and 102M-4C.

Then, the radiation source 100 emits a low-energy ray 102L when the time t has elapsed. At this time, the inspected object 103 has moved forward by a distance of one pixel, i.e., V*t. The low-energy ray 102L penetrate through the parts 3, 4 and 5 of the inspected object 103, and is subsequently collected and buffered by the first, second and third linear arrays 104a, 104b and 104c, respectively, with the detection values being referred as 102L-3A, 102L4B and 102L-5C. Thus, the transmission values of part 3 under three energy levels can be obtained, which are referred as 102H-3C, 102M-3B and 102L-3A.

Next, on the basis of the timing 203, the radiation source 100 generate a high-energy ray 102H again, while the inspected object 103 moves further by a distance of one pixel V*t. Therefore, the high-energy ray 102H interacts with the parts 4, 5 and 6 of the inspected object 103. After such interaction, the detection values are collected respectively by the first, second and third linear arrays 104a, 104b and 104c, and referred as 102H-4A, 102H-5B and 102H-6C. Subsequently, the transmission values of part 4 under three energy levels can be obtained, which are referred as 102H4A, 102M-4C and 102L-4B.

It should be noted the two linear arrays could be extended as six or nine linear arrays to increase scan speed.

The above-mentioned is only the specific embodiments of the present invention, while the scope of the present invention is not limited to it. Any modification or substitution, which is obvious to the skilled in the art within the technical range disclosed in the present invention, should be included in the scope of the present invention, which is thus defined by the claims.

What is claimed is:

1. A system for detecting x-rays comprising:
    a radiation source for generating x-rays forming a fan-shaped beam;
    a detector array comprising:
        a first linear array for detecting a first x-ray and a second x-ray which penetrate through a first plurality of parts of an object under inspection to acquire first values and second values for the first plurality of parts, wherein the second x-ray and the first x-ray are alternately emitted from the radiation source; and
        a second linear array arranged parallel to the first linear array for detecting the first x-ray and the second x-ray which penetrate through a second plurality of parts of the object to acquire third values and fourth values for the second plurality of parts, wherein the object moves relative to the radiation source and first and second linear array along a straight line substantially perpendicular to a plane in which the x-rays are arranged, and the at least one of first plurality of parts is the same as at least one of the second plurality of parts;
    processing module for matching the second to third detection values to obtain the detection values for the same parts of the first plurality of parts and the second plurality of parts under the first x-ray and the second x-ray.

2. The system of claim 1, wherein the first linear array is arranged in contact with the second linear array.

3. The system of claim 1, wherein the distance between the first linear array and the second linear array is adjustable.

4. The system of claim 3, wherein the distance is adjustable based on the moving speed of the object and the time interval between the alternate generation of the first x-ray and the second x-ray.

5. The system of one of claims 2 to 3, wherein each detector element of the first linear array and the second linear array comprises a scintillator or a gas detector.

6. The system of claim 5, wherein the scintillator is $CdWO_4$ or CsI.

7. The system of claim 5, wherein the first x-ray and the second x-ray are generated by a same radiation source.

8. A method of detecting x-rays forming a fan-shaped beam with a detector array comprising a first linear array and a second linear array arranged parallel to each other, the method comprising the steps of:
    generating from a radiation source alternately a first x-ray and a second x-ray to penetrate through an object under inspection;
    detecting the first x-ray and the second x-ray which penetrate through a first plurality of parts of the object with the first linear array, to acquire first values and second values for the first plurality of parts;
    detecting the first x-ray and the second x-ray which penetrate through a second plurality of parts of the object with the second linear array, to acquire third values and fourth values for the second plurality of parts, wherein the object moves relative to the radiation source and first and second linear array along a straight line substantially perpendicular to a plane in which the x-rays are arranged, and at least one of the first plurality of parts is the same as at least one of the second plurality of parts; and
    matching the second to third detection values to obtain the detection values for the same parts of the first plurality of parts and the second plurality of parts under the first x-ray and the second x-ray.

9. The method of claim 8 further comprises adjusting the distance between the first linear array and the second linear array based on the moving speed of the object and the time interval between the alternate generation of the first x-ray and the second x-ray.

10. The method of claim 9, wherein the first x-ray and the second x-ray are generated by a same radiation source.

11. The method of claim 8, wherein each detector element of the first linear array and the second linear array comprises a scintillator or a gas detector.

12. The method of claim 11, wherein the scintillator is $CdWO_4$ or CsI.

13. A system for detecting x-rays comprising:
a radiation source for generating x-rays forming a fan-shaped beam;
a detector array comprising:
   a first linear array for detecting a first x-ray, a second x-ray and a third x-ray which penetrate through a first plurality of parts of an object under inspection to acquire first values, second values and third values for the first plurality of parts, wherein the first x-ray, the second x-ray and the third x-ray are alternately emitted from the radiation source;
   a second linear array arranged parallel to the first linear array for detecting the first x-ray, the second x-ray and the third x-ray which penetrate through the second plurality of parts of the object to acquire fourth values, fifth values and sixth values for the second plurality of parts, wherein at least one of the first plurality of parts is the same as at least one of the second plurality of parts;
   a third linear array arranged parallel to the first linear array and the second linear array for detecting the first x-ray, the second x-ray and the third x ray which penetrate through a third plurality of parts of the object to acquire seventh values, eighth values and ninth values for the third plurality of parts, wherein the object moves relative to the radiation source and first and second and third linear array along a straight line substantially perpendicular to a plane in which the x-rays are arranged, and at least one of the second plurality of parts is the same as at least one of the third plurality of parts; and
processing module for matching the second and fourth detection values to obtain the detection values for the same parts of the first plurality of parts and the second plurality of parts under the first x-ray and the second x-ray, matching the third, fifth and seventh detection values to obtain the detection values for the same parts of the first plurality of parts and the second plurality of parts and the third plurality of parts under the first x-ray, the second x-ray and the third x-ray, and matching sixth and eighth detection values to obtain the detection values for the same parts of the second plurality of parts and the third plurality of parts.

* * * * *